United States Patent [19]

Armstrong et al.

[11] Patent Number: 4,797,095
[45] Date of Patent: Jan. 10, 1989

[54] ORTHODONTIC HOOK MOUNTING

[75] Inventors: Maclay M. Armstrong, Seattle; Steven A. Houser, Edmonds; Jeffrey A. Armstrong, Mercer Island, all of Wash.

[73] Assignee: Unitek Corporation, Monrovia, Calif.

[21] Appl. No.: 834,288

[22] Filed: Feb. 27, 1986

Related U.S. Application Data

[63] Continuation-in-part of Ser. No. 609,409, May 11, 1984, abandoned.

[51] Int. Cl.⁴ .................................................. A61C 3/00
[52] U.S. Cl. .......................................... 433/22; 433/18
[58] Field of Search ........................ 433/18, 19, 10, 11, 433/13, 14, 16, 17, 21, 22

[56]         References Cited
U.S. PATENT DOCUMENTS

| | | | |
|---|---|---|---|
| 2,104,192 | 1/1938 | Ford | 433/10 |
| 3,158,934 | 12/1964 | Waldman | 433/19 |
| 3,237,305 | 1/1966 | Hegedus | 433/21 |
| 3,391,461 | 7/1968 | Johnson | 433/17 |
| 3,508,332 | 4/1970 | Armstrong | 433/21 |
| 3,683,502 | 8/1972 | Wallshein | 433/22 |
| 3,686,758 | 8/1972 | Kesling | 433/18 |
| 3,871,096 | 3/1975 | Wallshein | 433/11 |
| 4,419,078 | 12/1983 | Pletcher | 433/11 |

*Primary Examiner*—John J. Wilson
*Attorney, Agent, or Firm*—Robert W. Beach; Ward Brown

[57]              ABSTRACT

A front body or plate for disposition in front of an arch wire is connected to a fork for disposition behind the arch wire by a crosstie forming a mounting that can be slid lengthwise of the arch wire to enable the fork to embrace the body of a tooth bracket behind the arch wire. A saddle projecting from the front body opposite the fork projects rearward to form a socket engageable with the arch wire by movement transversely of the arch wire. The prong of the fork nearer the rearward projection of the saddle may be shorter than the prong of the fork farther from the rearward projection to facilitate installation of the mounting.

20 Claims, 9 Drawing Sheets

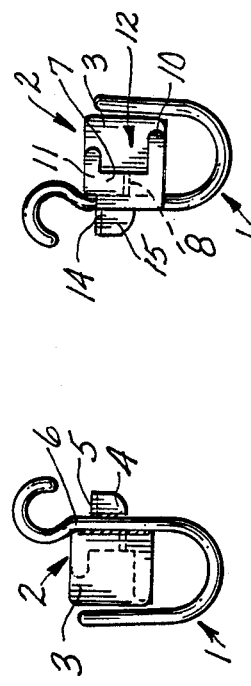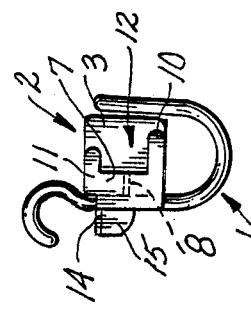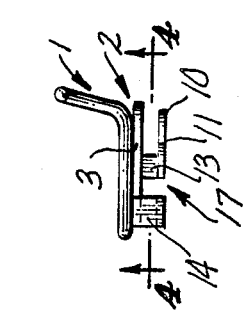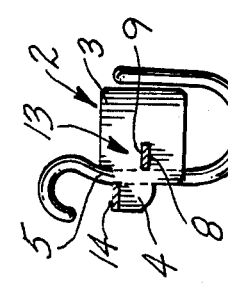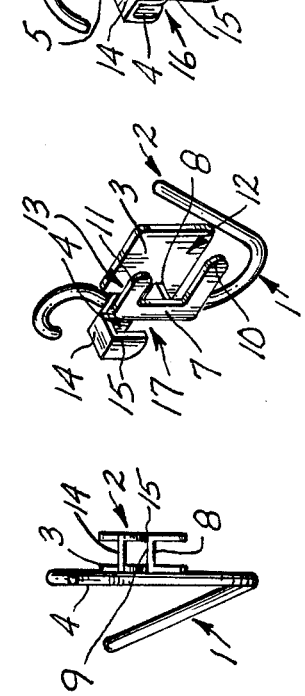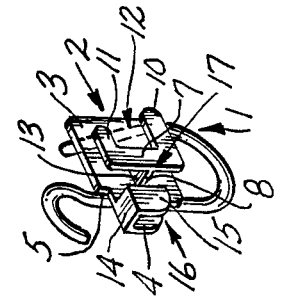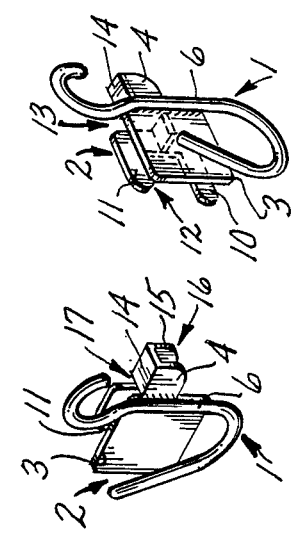

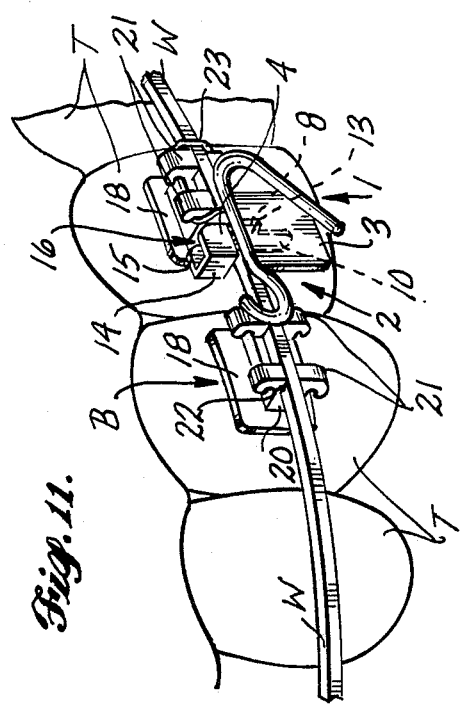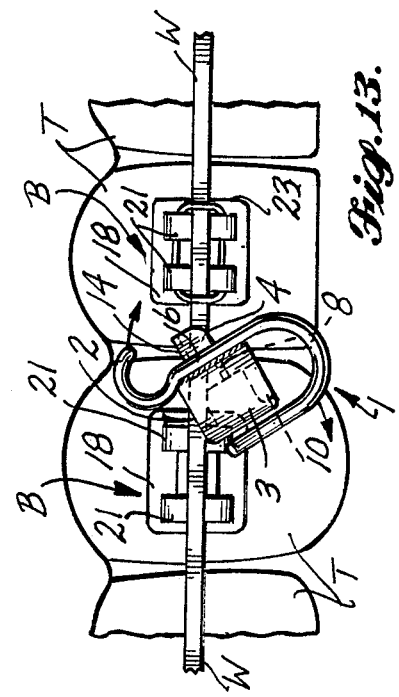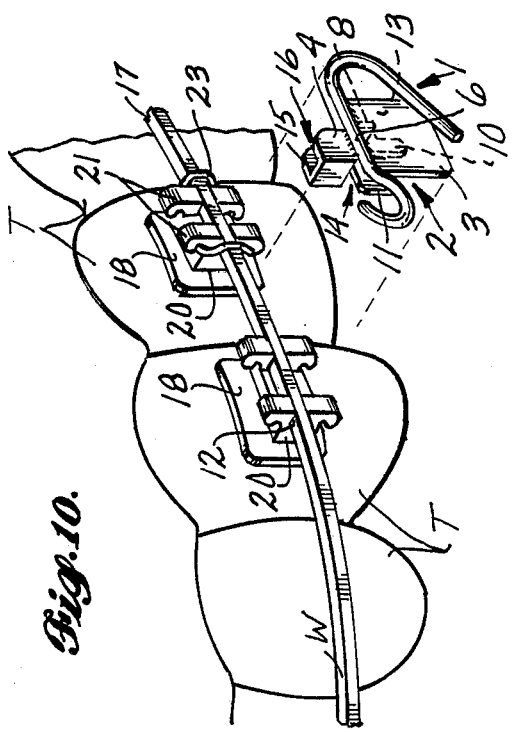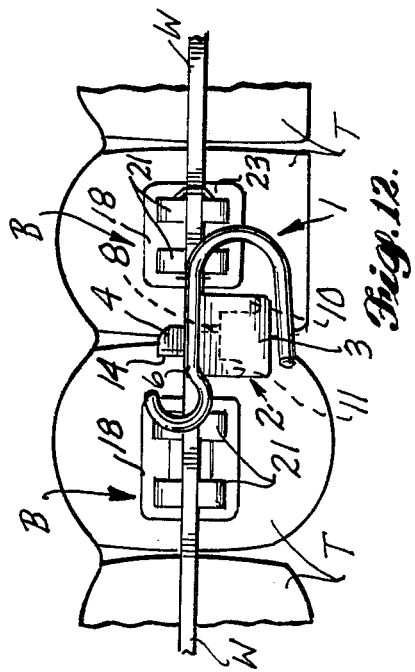

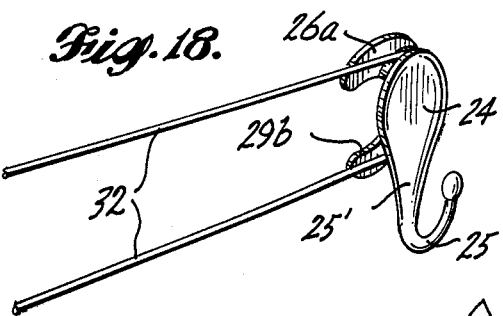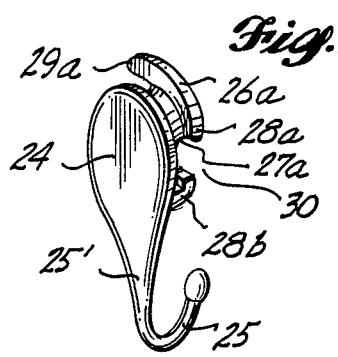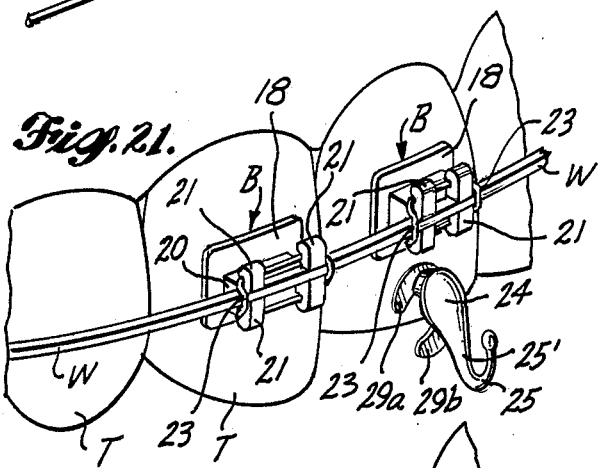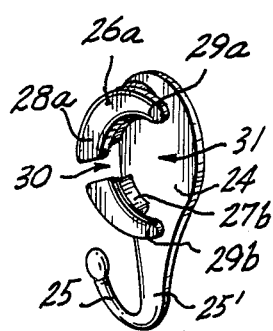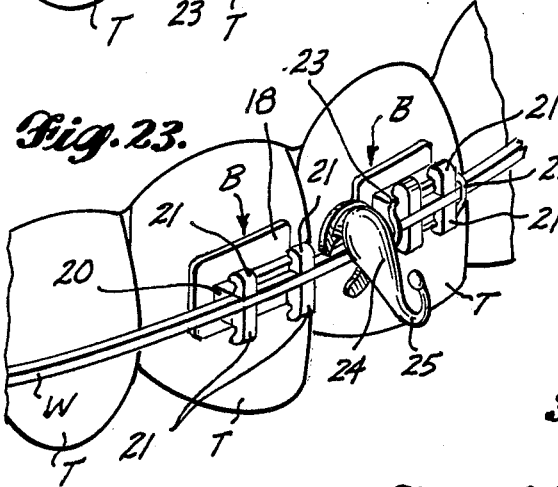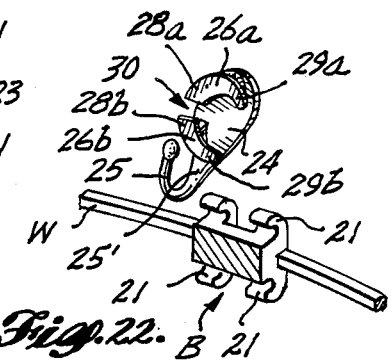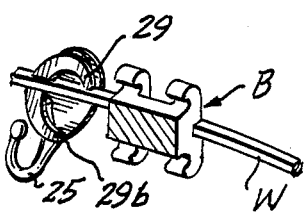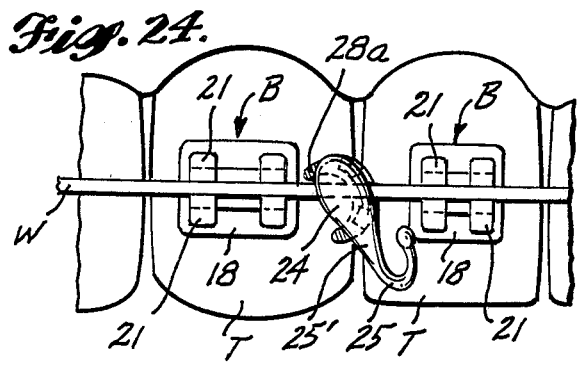

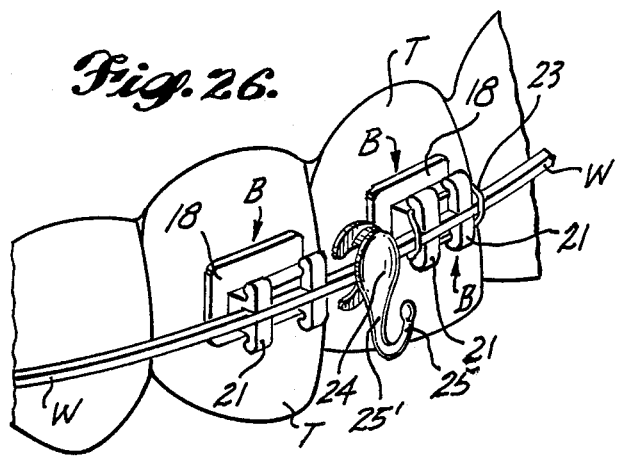
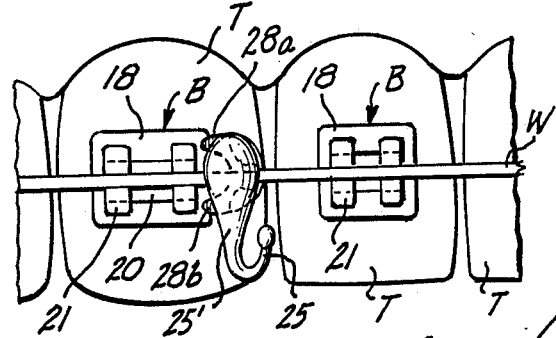
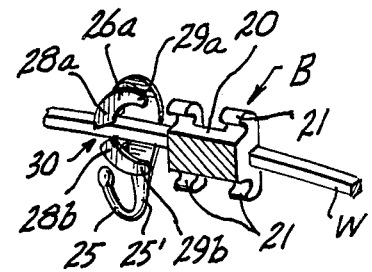
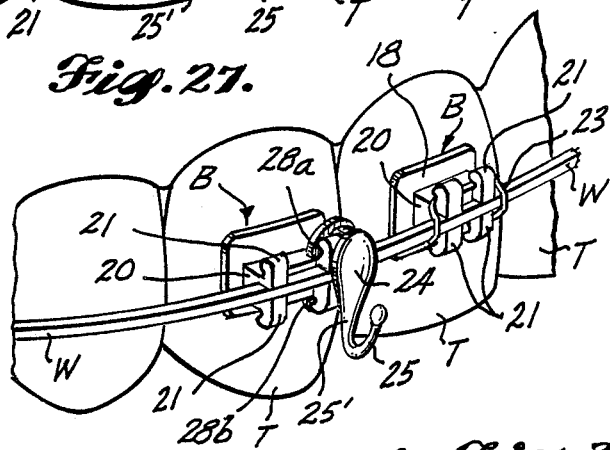
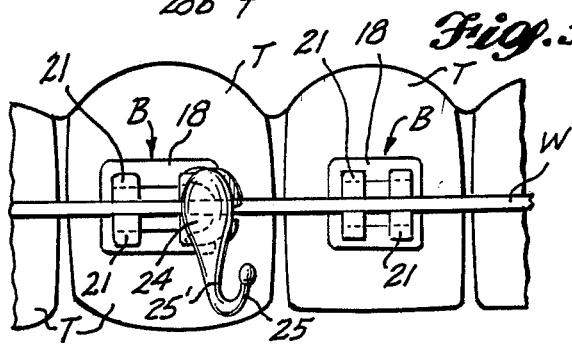
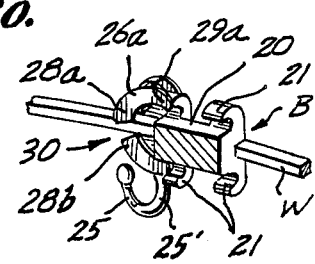

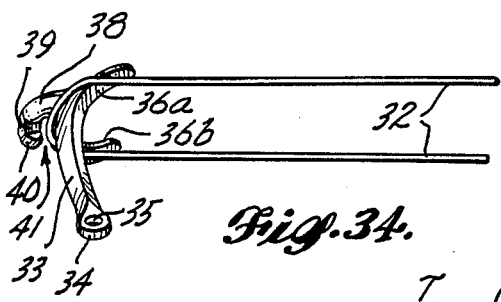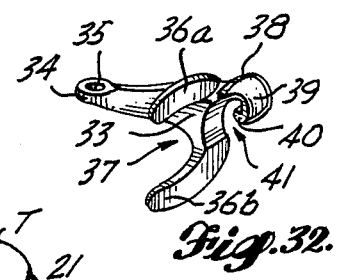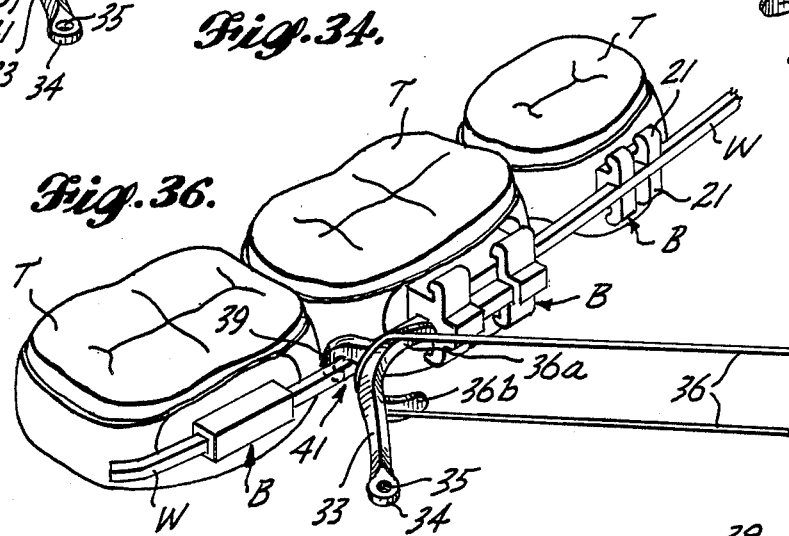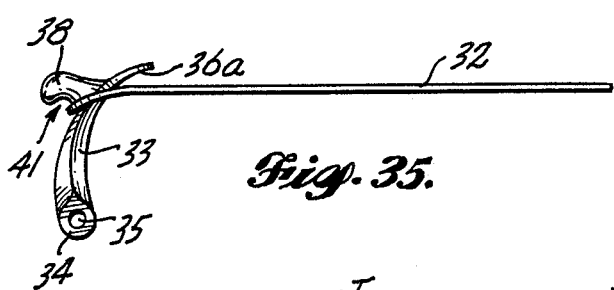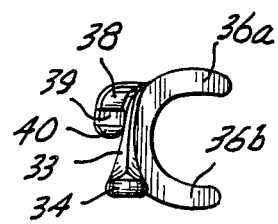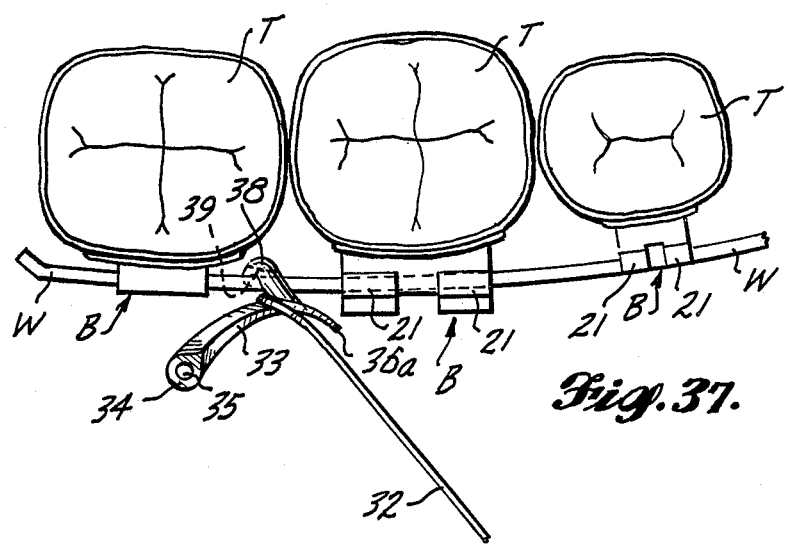

ORTHODONTIC HOOK MOUNTING

RELATED APPLICATION

This application is a continuation-in-part of patent application Ser. 609,409, filed May 11, 1984, now abandoned, for Orthodontic Hook Mounting.

BACKGROUND OF THE INVENTION

1. Field of the Invention

This invention relates to a mounting for an orthodontic hook or the like that can be applied to the assembly of an arch wire fitted in the arch wire groove of a tooth bracket.

2. Prior Art

Hooks have been secured to arch wires for use as anchoring devices for applying forces to the teeth, such as intermaxillary or intramaxillary springs, elastomeric modules or rubber bands. Usually such hooks have been secured to an arch wire by welding or silver soldering, as described, for example, in Armstrong U.S. Pat. No. 3,508,332, issued April 28, 1970, at column 1, lines 35 and 36. Customarily the hooks are attached to an arch wire by the manufacturer and consequently cannot be placed optimally for each patient. It is difficult for hooks to be attached to an arch wire at locations best suited for a particular patient by or for an orthodontist because great skill is required to weld or solder a hook to an arch wire without such operation inadvertently annealing the arch wire. An arch wire which has become annealed has lost its ability to transmit orthodontic forces effectively to the teeth to which the brackets carrying the arch wire are bonded.

Arch wires are custom-fitted to a particular patient by the orthodontist and after a period of treatment it may be desirable to apply a pull or a torque on an arch wire at a particular location. In such case it is desirable to apply a hook to the fitted arch wire at that particular location but it is difficult to make a good soldered joint to attach such a hook if the parts being soldered are not perfectly clean and dry. Cleanliness is difficult to insure for an arch wire that has been in a mouth for any appreciable period of time. A dirty arch wire will require heating to a higher temperature in the hook-attaching operation which increases the risk of annealing the arch wire.

If a poor welded or soldered joint is made, the hook can be pulled from the arch wire because it is subjected to considerable stress by the orthodontic treatment force. If the arch wire is inadvertently annealed as a result of the hook-attaching operation, it may break or bend and lose the resiliency required to transmit orthodontic forces effectively between the teeth to which it is attached by tooth brackets for moving such teeth. On the other hand, if the hook is securely attached to the arch wire, it is difficult to remove the hook at the end of the treatment requiring application of force to a hook, or when it is necessary to relocate the hook, and the arch wire may be impaired or damaged excessively by such removing operation.

During the progress of orthodontic treatment it may be desirable to replace the arch wire with an arch wire of different cross-sectional size and/or shape. Each time the arch wire is changed a new set of hooks is required. Also, depending on the progress of the orthodontic treatment, it may be desirable to apply force to arch wire hooks at different times. Frequently, hooks interfere with the adjustment of an arch wire to accomplish a particular treatment and it is therefore undesirable to have hooks on an arch wire when they are not being used.

Alternatively, hooks have been mounted on caps engageable with orthodontic brackets, as described in Johnson U.S. Pat. No. 3,391,461, issued July 9, 1968, at column 2, lines 24 and 25. A principal difficulty with such a hook mounting is that it is necessary to hold the cap in place to restrain sliding of it relative to the tooth bracket by bending retaining tabs to engage the bracket, which may require that stress be exerted on the tooth bracket that is uncomfortable or even distressing to the patient. If the cap is to be removed, the tabs must be unbent which, again, can produce an undesirable stress on the tooth bracket.

The Waldman U.S. Pat. No. 3,158,934, issued Dec. 1, 1964, shows in FIG. 10 an orthodontic appliance for attachment to an arch wire having two hooks 32 to which springs or rubber bands, presumably, may be attached. Such appliance, however, has a slot 22 positioned to receive the arch wire 14 when the arch wire is parallel to the rear wall 20 forming the slot bottom, as shown in FIG. 2. The appliance is secured to the arch wire by tightening a very small set screw such as 19 in FIG. 1 or 119 in FIG. 2. Such an appliance is anchored directly to the arch wire and is not engaged with a tooth bracket.

SUMMARY OF THE INVENTION

A principal object of the present invention is to provide a hook or attachment mounting for an orthodontic arch wire that can be applied to an arch wire held by teeth brackets easily and quickly and which mounting can be removed with equal facility.

Specifically, the installation of the mounting does not require any welding or soldering operation, nor does it require that any part of the mounting or of the arch wire or bracket be deformed.

A further object is to provide such a mounting which is strong and retained in place securely.

An additional object is to provide a hook or attachment mounting which will transmit orthodontic forces effectively to an orthodontic arch wire for distribution to a number of teeth to which the arch wire is secured instead of the reaction force from a tooth to be repositioned being applied to only a single tooth even though the hook mounting is not directly fixed on the arch wire.

It is also an object to provide a hook or attachment mounting which will minimize the tendency of the orthodontic force to bend or deform the arch wire or tooth bracket.

An object is to provide a mounting which can be utilized for a variety of hook shapes.

Another object is to provide a type of hook or attachment mounting which can be applied to an arch wire and bracket assembly at any location, either on the upper arch or the lower arch, and at any position circumferentially of the arch.

An incidental object is to provide a hook mounting which will act to retain an arch wire in the arch wire-receiving slot of a tooth bracket.

A further object is to provide a mounting for an orthodontic hook or attachment which is compact and unobtrusive and is in place on the arch wire only when it is being utilized in the orthodontic treatment so as to minimize inconvenience to the orthodontist and to the patient.

An advantage of the hook or attachment mounting is that it can be reused virtually indefinitely.

The foregoing objects can be accomplished by an orthodontic hook or attachment mounting having a fork straddling the body of a tooth bracket and, preferably, having at least one socket to receive a portion of the arch wire adjacent to the tooth bracket. The shank of a hook of any desired shape or other attachment can be fixed to the mounting such as by welding or silver soldering, or the hook or attachment can be formed as an integral part of the mounting.

BRIEF DESCRIPTION OF THE DRAWINGS

FIG. 1 is a front elevation of the hook mounting carrying a representative type of hook.

FIG. 2 is a rear elevation of the hook mounting.

FIG. 3 is a plan of the hook mounting.

FIG. 4 is a vertical section through the hook mounting taken on line 4—4 of FIG. 3.

FIG. 5 is a side elevation of the hook mounting.

FIG. 6 is a top rear perspective of the hook mounting viewed from one side, and FIG. 7 is a top rear perspective of the hook mounting viewed from the opposite side.

FIG. 8 is a top front perspective of the hook mounting viewed from one side, and FIG. 9 is a top front perspective of the mounting viewed from the opposite side.

FIG. 10 is an exploded top perspective of a hook mounting and an arch wire and tooth bracket installation at a location where the mounting is to be installed, and FIG. 11 is a similar view showing the hook mounting in an initial position during the installation procedure.

FIG. 12 is a front elevation of the hook mounting and arch wire and tooth bracket assembly with the parts in the initial position illustrated in FIG. 11.

FIG. 13 is a front elevation of the hook mounting and of the arch wire and bracket assembly showing the hook mounting in an intermediate relationship to the arch wire and bracket during installation.

FIG. 18 is a top front perspective of an anterior hook mounting of a different type viewed from one side and a securing wire.

FIG. 19 is a top front perspective of the same hook mounting viewed from the other side.

FIG. 20 is a top rear perspective of the same hook mounting.

FIG. 21 is a top front perspective of the different type of anterior hook mounting in relationship to an arch wire.

FIG. 22 is a top rear perspective of the same hook mounting shown in relationship to an arch wire.

FIG. 23 is a top front perspective of the different type of anterior hook mounting shown in a different relationship to the arch wire.

FIG. 24 is a front elevation of the same hook mounting shown in the same relationship to the arch wire.

FIG. 25 is a top rear perspective of the hook mounting shown in the same relationship to the arch wire.

FIG. 26 is a top front perspective of the different type of anterior hook mounting shown in still a different relationship to the arch wire.

FIG. 27 is a top rear perspective view showing the hook mounting in such different relationship to the arch wire.

FIG. 28 is a front elevation of the same hook mounting shown in a further relationship to the arch wire.

FIG. 29 is a top rear perspective of the same hook mounting shown in still a further relationship to the tooth bracket.

FIG. 30 is a top front perspective of the different type of anterior hook mounting shown in a final relationship to the tooth bracket.

FIG. 31 is a front elevation of the same hook mounting shown in such final relationship to the tooth bracket.

FIG. 32 is a top rear perspective of a posterior modified orthodontic attachment.

FIG. 33 is an end elevation of such posterior modified attachment.

FIG. 34 is a top perspective of such posterior modified attachment viewed from an end in conjunction with a securing wire.

FIG. 35 is a plan of such attachment in conjunction with a securing wire.

FIG. 36 is a top front perspective of the posterior modified attachment and securing wire shown in an initial assembled relationship to an arch wire.

FIG. 37 is a plan of such attachment and securing wire shown in such initial assembled relationship to an arch wire.

DETAILED DESCRIPTION

Figure 15:
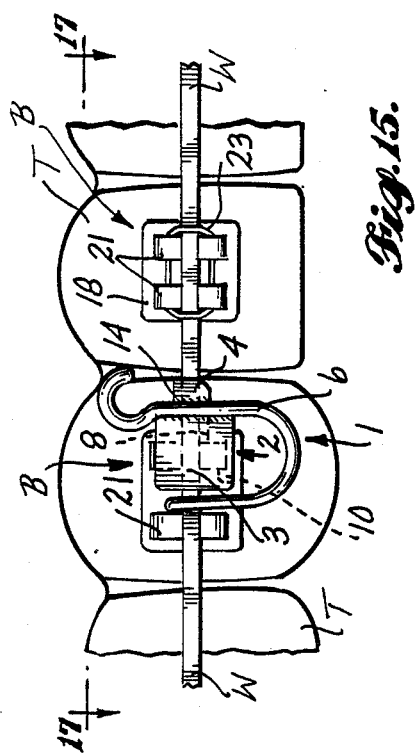
FIG. 15 is a similar view showing the mounting installed on the arch wire and tooth bracket assembly.

An orthodontic hook 1 for applying a pull or a torque to a tooth can be of a variety of shapes. Consequently, the hook of the shape shown in the drawings should be considered to be merely representative. The mounting 2 for such hook should be capable of being installed on a tooth bracket B and arch wire assembly at virtually any location around either the upper or lower tooth arch. Also the mounting is capable of applying a pull or torque primarily to the arch wire W and secondarily to a bracket B carrying the arch wire and attached to a particular tooth T. Application of force only or primarily to a single tooth could cause undesirable rotation or displacement of such tooth.

The mounting 2 is made principally of small flat or plate components that may be integrated by being parts of a unitary casting. It is preferred that the casting be made of stainless steel or other strong, durable, noncorrosive and nontoxic material. The mounting includes a front plate or body 3 which may be substantially square and have a width of the order of ⅛ inch (3.175 mm) such as being from 0.1 to 0.2 inch (2.5 to 5.0 mm) and a thickness of 0.01 to 0.02 inch (0.25 to 0.5 mm).

Preferably the front plate has a tongue 4 projecting from one edge, which edge will be disposed substantially vertical when the mounting is installed on a tooth bracket and arch wire assembly. The hook 1 is attached to the plate or body 3 at the root 5 of tongue 4 with its shank 6 upright, as shown in FIG. 1, or may be cast as a unitary part of the mounting. The hook shank is bonded to the front of the front plate by any suitable means such as welding, silver solder or suitable adhesive. The hook may have hooked ends at opposite sides of the shank 6.

The mounting 2 has at least one element bearing on the arch wire W to transmit force to it and some structure for holding the mounting in proper relation to the arch wire. For this purpose a rear plate 7 is located parallel to the front plate 3 and connected to it by a crosstie 8 having a surface 9 constituting an abutment for bearing on the arch wire W disposed substantially perpendicular to the hook shank 6 and forming the planar bottom of an upwardly-opening socket 13 between the front plate 3 and the rear plate 7 which embraces the arch wire.

The rear plate 7 of the mounting has at least one prong engaging the tooth bracket body and preferably is shaped as a fork having substantially parallel prongs. It is desirable for one prong 10 to be longer than a shorter prong 11. Such prongs are spaced apart to provide a notch 12 between them for straddling the bracket B to deter roll of the hook relative to the arch wire W. The crosstie 8 is located relative to the rear plate fork such that its surface 9 closer to the shorter prong 11 is located closer to the longer prong 10 than to the shorter prong 11 as shown in FIG. 2 so as to provide a deeper socket 13 above its surface 9 than would be formed if the crosstie were centered between the prongs of the fork.

The edge of tongue 4 nearer the shorter prong 11 carries a rearward projection 14 constituting an abutment for bearing on the arch wire W. The end of such projection remote from the tongue preferably carries a further projection or lip 15 extending toward the longer prong 10 to form with the rearward projection 14 a return bent channel-shaped reaction and retention saddle forming a socket 16 for embracing the arch wire W which opens in the direction opposite the opening of the socket 13 between the front plate 3 and the rear plate 7 and having a planar bottom formed by the projection 14 parallel to the surface 9. A rearwardly-opening slot 17 is formed behind the front plate 3 adjacent to the tongue root 5 and between the rear plate 7 and crosstie 8 on one side and the rearward projections 14 and 15 on the other side as shown in FIGS. 2 and 3. Such slot forms an angle with the socket bottoms 14 and 13 so that the arch wire W cannot enter such slot when the arch wire is substantially parallel to such socket bottoms but such slot can receive the arch wire only when it is in registration with the arch wire by being at a substantial angle to such socket bottoms.

The hook mounting 2 is constructed for installation on a conventional orthodontic assembly of an arch wire W carried by brackets B attached to the front faces of the teeth. Each tooth bracket includes a base 18 bonded to the outer surface of a tooth T. A body 20 projects outward from the bracket base and carries a plurality of wings 21 projecting upward and downward from opposite sides of a groove or slot 22 between them in which the arch wire W is fitted. Normally, the arch wire is tied to each tooth bracket by an elastomeric ring or a fine wire 23, as shown best in FIGS. 10 and 16. The arch wire and hook mounting may be tied to the bracket by such a tie wire or elastomeric ring after the hook mounting has been installed, but also the socket 13 of such mounting will function to retain the arch wire W in the slot 22 of such bracket.

The hook mounting 2 is installed on the arch wire and bracket assembly at virtually any location around the tooth arch by a manipulation involving sequential translation, swiveling and sliding steps without deforming any parts of such assembly or of the mounting. To install the mounting, it is positioned relative to the arch wire and tooth bracket assembly with its rearwardly-opening slot 17 generally in registration with the arch wire as illustrated in FIG. 10. As a first installation step the mounting is then translated toward a portion of the arch wire W located between adjacent tooth brackets B until the arch wire is received in the rearwardly-opening slot 17 of the mounting when it is in the position shown in FIG. 11 with the arch wire at a substantial angle to the abutment and planar bottom surface 9 of the socket 13 formed by crosstie 8 and rear plate 7 and at a similar substantial angle to the abutment and planar bottom surface of the socket 16 formed by rearward projection 14 and lip 15. Such translation is continued until the rearward side of the front plate 3 abuts the front surface of the arch wire.

Figure 14:
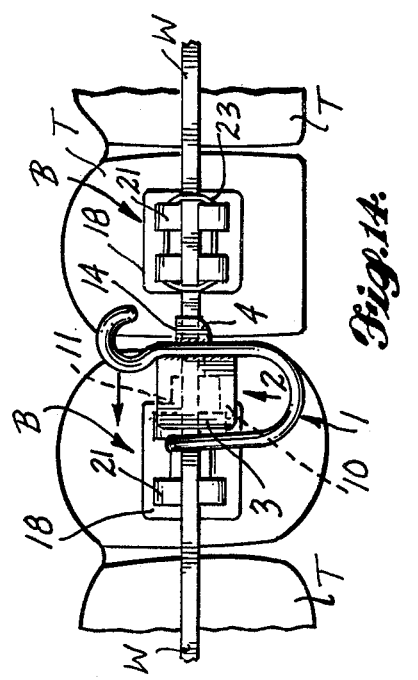
FIG. 14 is a similar view showing the hook mounting in a further intermediate position.
Figure 17:
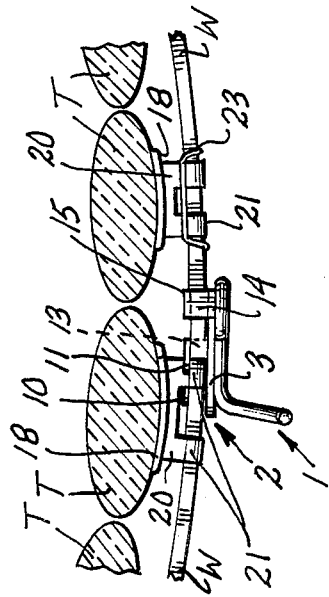
FIG. 17 is a plan of the hook mounting installed on the arch wire and tooth bracket assembly as seen from line 17—17 of FIG. 15.

Next, as a second step, the mounting is swiveled clockwise as seen in FIGS. 12 and 13 through an angle of 90 degrees from the position shown in FIGS. 11 and 12 to the latched position shown in FIG. 14 in which the saddle notch 16 has been moved to embrace the portion of the arch wire at one side of the root 5 of tongue 4, and the socket 13 between the front plate 3 and the rear plate 7 has been moved to embrace the portion of the arch wire at the side of the tongue root 5 opposite the rearward projection 14. Prong 11 of the rear plate is short enough so that its end will pass the body 20 of the adjacent tooth bracket B as the mounting is thus swiveled when the mounting is located between adjacent tooth brackets B holding the arch wire.

Figure 16:
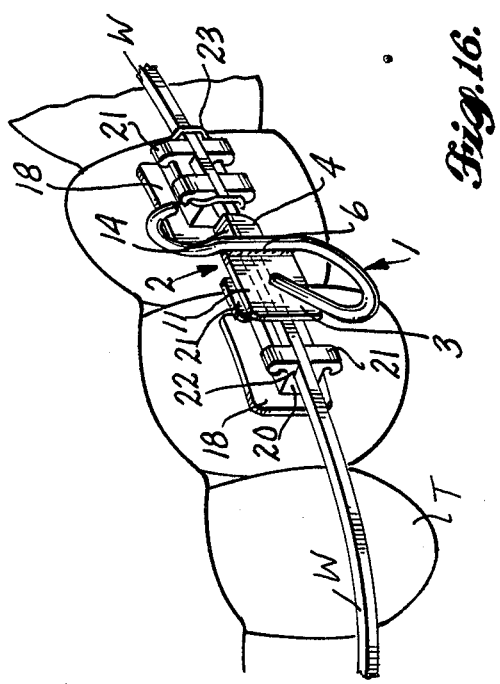
FIG. 16 is a top perspective of the hook mounting shown installed on the arch wire and tooth bracket assembly.

The third step required to complete the installation of the mounting 2 on the arch wire and tooth bracket assembly is to slide the mounting along the arch wire W to the left as seen in FIG. 14 from the position shown in FIG. 14 to the position of FIGS. 15 and 16. Such sliding action will move the prongs 10 and 11 astride the body 20 of the tooth bracket. In such installed position, the mounting can no longer be swiveled in either direction or tilted appreciably relative to the tooth bracket or the arch wire. Such swiveling will be prevented by engagement of one or the other of the prongs 10 and 11 with the upper or lower side of the bracket body 20. The hook mounting can be retained positively in such position either by tying the mounting in place appropriately with a tie wire 23 or an elastomeric ring or by the pulling force exerted on the hook 1 by an elastic band or a spring anchored to the hook in the manner shown in FIG. 44.

A pull exerted in the proper direction on the hook 1 will be transmitted directly to the arch wire W on which surface 9 and saddle socket 16 bears. The pulling force exerted on the hook may be in a direction tending to swivel the hook, which will exert a torque on the arch wire by the saddle bottom projection 14 bearing on it. In such case, such projection serves as a reaction outrigger.

Just as the hook mounting 2 can be installed on an arch wire and tooth bracket assembly without deforming any parts of such assembly or of the mounting, as described above, the hook mounting can be removed from the arch wire and tooth bracket assembly by following a procedure which is the reverse of the installation procedure described above, again without deforming any portion of the arch wire and tooth bracket assembly or of the mounting. To remove the hook mounting, it is only necessary first to slide the mounting to the right as seen in FIG. 15 to withdraw the rear plate fork from the bracket body 20, such as by moving the mounting from the position shown in FIG. 15 to the position shown in FIG. 14. The mounting can then be swiveled counterclockwise relative to the arch wire and tooth bracket assembly through the position shown in FIG. 13 to the position shown in FIGS. 11 and 12 in which the slot 17 is in registration with the arch wire W. From this position shown in FIGS. 11 and 12, the mounting can be translated toward the position shown in FIG. 10 to free the rearwardly-opening slot 17 of the mounting from the arch wire.

While the arch wire W shown in the drawings is of square cross section, the hook mounting 2 can be assembled as readily with an arch wire and tooth bracket assembly incorporating an arch wire of circular cross section. Moreover, it is not necessary that the parts of the mounting described above, including the socket 13 and the saddle notch 16, fit the arch wire snugly, so that such mounting can be applied to assemblies having arch wires of different sizes.

Also, while the structure has been described as constituting a mounting for an orthodontic hook, any other type of member, such as an eye, a tube or a knob, could be attached to the front plate 3 in place of the hook 1 if desired.

It is preferable to provide different types of attachments for specific orthodontic purposes. The attachments shown in FIGS. 18 to 44 are particularly adapted for use in correcting an overbite condition or reducing the spacing between adjacent side teeth in an upper jaw. Thus the anterior hook shown in FIGS. 18 to 31, inclusive, can be applied in an anterior position on the right side of the upper tooth arch whereas the posterior attachment shown in FIGS. 34 to 43 can be attached to the arch wire in a lower posterior position at the right side of the mouth. Hook and attachment devices which are mirror images of those shown can be shaped specially for corresponding attachment to the upper and lower arch wires at the left side of the mouth.

The anterior orthodontic hook shown in FIGS. 18 to 31 is designed to be installed in the upper right side of the mouth near the front as indicated in FIGS. 21 and 23. The hook mounting includes a front plate 24 carrying a depending hook 25 connected to the front plate by a shank 25'.

The front plate 24 carries a divided rear plate composed of an upper plate section 26a and a lower plate section 26b. Such rear plate sections are attached in spaced parallel relationship to the front plate 24 by crossties 27a and 27b, respectively. The rear plate sections are preferably curved, having concave edges facing each other. At least one of the corresponding ends 28a and 28b, preferably 28a, overhangs its crosstie 27a, and end 28b may correspondingly overhang its crosstie 27b to some extent. The opposite corresponding ends 29a and 29b of the rear plates project farther beyond the crossties 27a and 27b to form prongs.

The ends 28a and 28b of the rear plate sections are spaced apart to form a slot 30 of a width at least slightly greater than the width of the arch wire W and of a depth such that the distance between the underside of the overhanging end 28a and the back of the front plate 24 slightly exceeds the thickness of the arch wire W.

The prongs 29a and 29b generally diverge from the overhanging end portions 28a and 28b of the rear plate sections to form a notch 31 between the ends of the prongs that can engage bracket bases of different widths.

To retain the orthodontic hook on an arch wire and bracket combination, it may be desirable to provide a tie wire 32, shown in FIG. 18, with the hook, a loop of which tie wire encircles the sides of the crossties 27a and 27b adjacent to the rear plate ends 28a and 28b and the free ends of the tie wire project from the hook mounting generally parallel to and in the same direction that the prongs 29a and 29b project from the hook mounting.

The slot 30 between the rear plate section ends 28a and 28b extends at an angle of approximately 60 degrees to the hook shank 25' so that, during installation of the hook mounting on the arch wire, the mounting is swivelled approximately 30 degrees between reception of the arch wire in the slot 30 and the final latched relationship between the hook mounting and the arch wire. The notch 31 between the prongs 29a and 29b of the rear plate sections 28a and 28b is at least as great as the thickness of the body 20 of a tooth bracket.

The sequential steps for installing an orthodontic hook mounting on an arch wire and tooth bracket assembly are illustrated generally in the sequence of FIGS. 21 to 31. Initially the hook shank 25' is canted relative to the arch wire W as shown in FIGS. 21 and 22 and the slot 30 is brought into registration with a section of the arch wire W between two adjacent tooth brackets B. The hook mounting is then translated toward the arch wire from the position shown in FIGS. 21 and 22 to the position shown in FIGS. 23, 24 and 25 in which the mounting slot 30 embraces the arch wire. When the hook mounting has been translated inward sufficiently far with the hook shank in canted position so that the overhanging end 28a of the rear plate section 26a passes inwardly beyond the arch wire, the hook mounting can be swiveled relative to the arch wire from the canted position shown in FIGS. 24 and 25 to the position shown in FIGS. 26, 27 and 28 in which the hook shank 25' is disposed in a plane substantially perpendicular to the arch wire. By such movement the overhanging end 28a of the rear plate section 26a is lodged behind the arch wire W so as to prevent forward translation of the hook mounting away from the arch wire. Such engagement of the overhanging end 28a of the rear plate section 26a behind the arch wire is shown best in FIG. 27.

Figure 44:
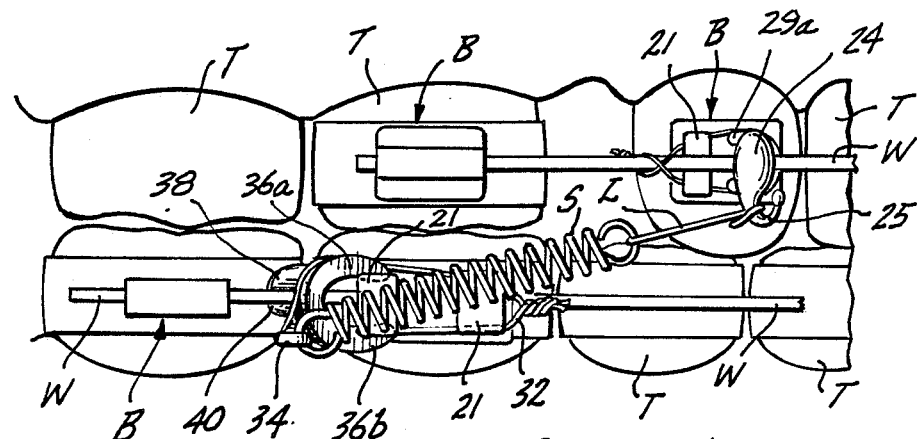
FIG. 44 is an elevation of side portions of upper and lower sets of teeth showing the anterior hook mounting of FIG. 26 connected to the posterior attachment mounting of FIG. 42 by a force-applying spring.

With the hook mounting in such latched relationship to the arch wire, the prongs 29a and 29b are located respectively generally higher and lower than the body 20 of an adjacent tooth bracket B as shown best in FIG. 28. Consequently the hook mounting can be shifted to the left relative to the adjacent tooth bracket through the position shown in FIG. 29 into the final position shown in FIGS. 30 and 31. In this position the prongs 28a and 28b are located behind the adjacent upper and lower wings 21 of the tooth bracket and the body between such wings is received in the notch 31 between the upper and lower prongs 29a and 29b. The free ends of the tie wire 32 may extend from the hook mounting alongside the body 20 of the tooth bracket behind the other set of upper and lower wings 21 of such bracket and may then be bent around such ears forward of the arch wire W and twisted together to prevent the hook mounting from being moved to the right, as seen in FIGS. 30 and 31, to withdraw the prongs 28a and 28b from behind the wings of the tooth bracket. The hook mounting is thus locked in place relative to the arch wire and tooth bracket assembly. Force may then be applied to the hook 25 by engaging with it a ligature or spring generally as shown in FIG. 44.

A posterior attachment suitable for installing on the lower arch wire W adjacent to a molar is shown in FIGS. 32 to 44. Such attachment includes a body 33 from which an arm 34 projects forwardly. The end of such arm is sufficiently large to have in it an eye 35 in which can be anchored a ligature wire or the end hook of a force-producing tension spring, or a force-producing elastomeric member.

From the body 33 project generally parallel prongs 36a and 36b designed to anchor the attachment relative to an arch wire and tooth bracket assembly. The free ends of such prongs are spaced apart to provide a notch 37 of a width sufficient to receive between the prongs the body 20 of a tooth bracket B.

From the body 33 of the attachment a reaction and retention saddle projects generally in the direction opposite the direction in which the prongs 36a and 36b project from the body. Such saddle includes a root projection 38 from the end of which remote from the body 33 projects an intermediate portion 39 at an angle to the root portion 38, which intermediate portion 45 carries a lip portion 40, making an angle with the intermediate portion 39. The three portions 38, 39 and 40 cooperatively form a hook-shaped saddle, as shown best in FIG. 34. The lip portion 40 spaced sufficiently from the body 33 of the attachment to provide a socket 41 for receiving an arch wire W by movement of the saddle transversely of the arch wire. As shown in FIG. 34, a ligature wire 32 may be supplied with the attachment for anchoring the attachment to an arch wire and tooth bracket assembly when the attachment has been installed on such assembly.

The procedure for installing an attachment such as shown in FIGS. 32, 33 and 34 on an arch wire and tooth bracket assembly is illustrated in FIGS. 36 to 43. First, with its body canted at an angle to the arch wire as shown in FIG. 36, the attachment is moved downward from a position above the arch wire W with the reaction and retention saddle 38, 39 and 40, located so that its socket 41 is fitted over the arch wire. During such movement the prongs 36a and 36b are disposed forward of the arch wire as shown in FIG. 37.

Figure 38:
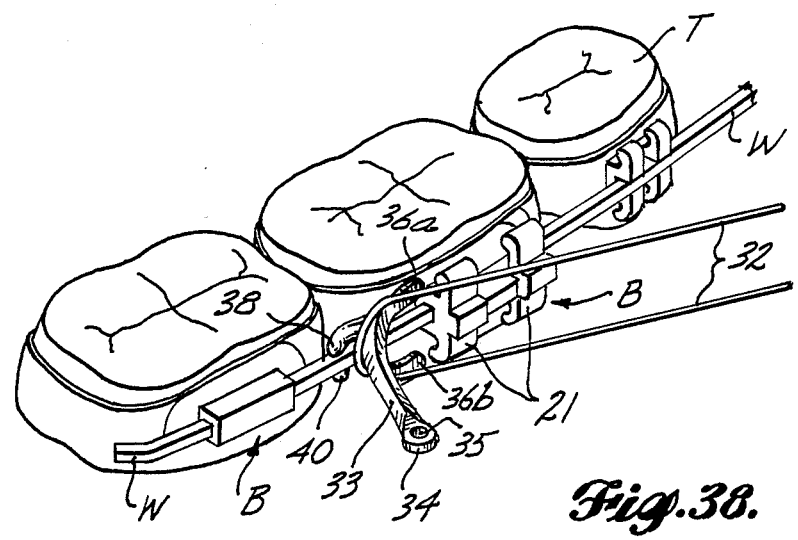
FIG. 38 is a top front perspective of the posterior modified attachment shown in a further assembled relationship to an arch wire.
Figure 39:
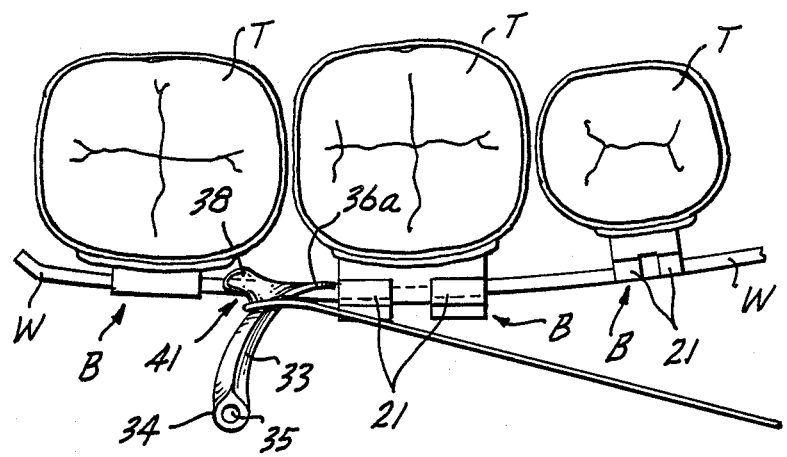
FIG. 39 is a plan of such attachment and securing wire shown in such further assembled relationship to the arch wire.

Next, the body of the attachment is swung from its position canted relative to the arch wire, shown in FIGS. 36 and 37, toward a position nearly perpendicular to the arch wire as shown in FIGS. 38 and 39, by which movement the notch 37 between the prongs 36a and 36b is moved transversely across the arch wire as indicated in FIGS. 38 and 39 until the prongs are located rearwardly of the arch wire and the notch 37 opens toward the body 20 of an adjacent tooth bracket B. The body 33 can then be swung farther until it is substantially perpendicular to the arch wire as shown in FIGS. 40 and 41 and the prongs 36a and 36b can engage behind the adjacent wings 21 of the adjacent bracket B.

Next, the attachment is shifted to the right from the position shown in FIGS. 38 and 39 to the position shown in FIGS. 40 to 43, inclusive, in which the prongs 36a and 36b straddle the tooth bracket body 20. With the attachment in that position it may have limited inward movement, but engagement of the saddle 38, 39, 40 with the rear of the arch wire, and engagement of the prongs 36a and 36b with wings 21 of the tooth bracket, will limit outward movement of the attachment relative to the arch wire and tooth bracket assembly.

Figure 40:
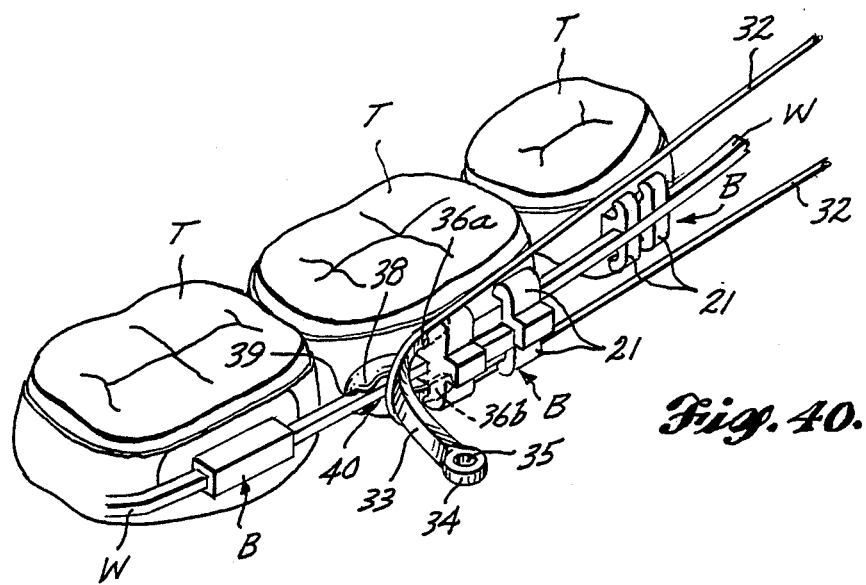
FIG. 40 is a top front perspective of the posterior modified attachment and securing wire shown in a still further relationship to the arch wire.
Figure 41:
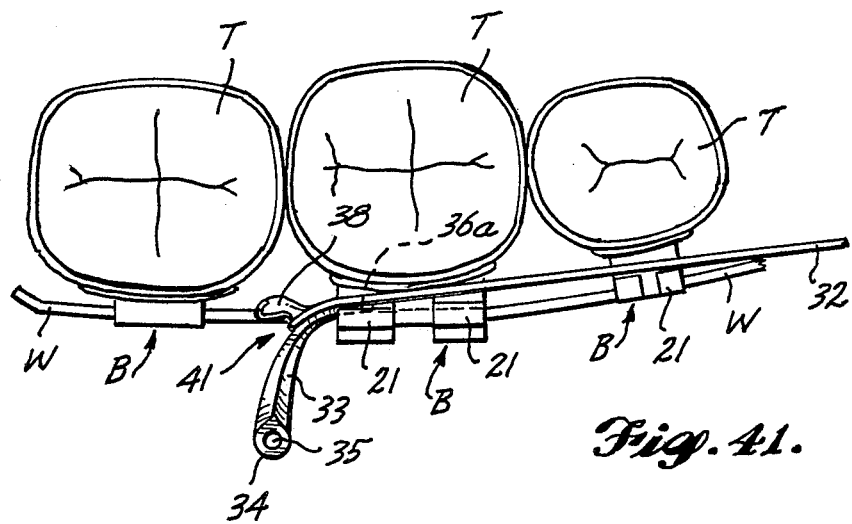
FIG. 41 is a plan of such attachment and securing wire shown in such still further relationship to the arch wire.
Figure 42:
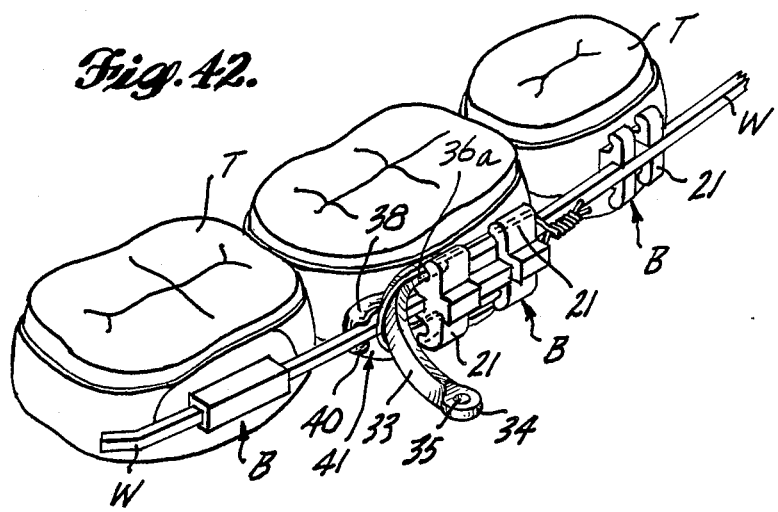
FIG. 42 is a top front perspective of the posterior modified attachment shown in its final relationship to the arch wire with the securing wire secured.
Figure 43:
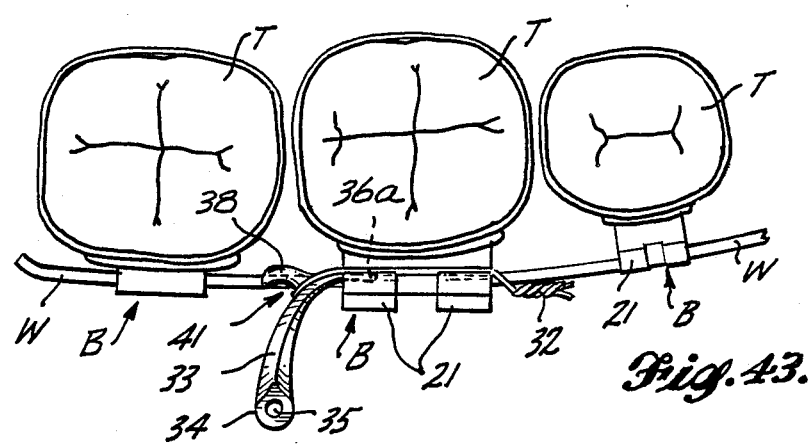
FIG. 43 is a plan of such attachment in its final relationship to the arch wire with the securing wire secured.

When the attachment has been moved into its final position relative to the arch wire and tooth bracket assembly as shown in FIGS. 40 and 41 it may be secured in such position with the ligature wire 32. As shown in FIGS. 40 and 41, the free ends of such ligature wire pass behind the upper and lower wings 21 respectively of the tooth bracket. The free ends of such ligature wire may then be twisted together outwardly of the arch wire W as shown in FIGS. 42 and 43 to prevent the attachment from being shifted to the left relative to the arch wire and tooth bracket assembly.

With an anterior orthodontic hook such as shown in FIGS. 1 to 33 installed on an upper arch wire and tooth bracket assembly in the position shown in the upper portion of FIG. 44 and a posterior orthodontic attachment such as shown in FIGS. 34 to 43 installed on the corresponding lower posterior arch wire and tooth bracket assembly as shown in the lower portion of FIG. 44, such anterior hook assembly and posterior attachment can be connected by a force-producing device such as a helical tension spring as shown in FIG. 44. In that figure, the lower posterior attachment is shown attached to the assembly between the first and second molars and the anterior hook is shown attached to a bracket on the first bicuspid, the second bicuspid having been removed. The rearward end of the upper arch wire is shown as being anchored to the first upper molar.

FIG. 44 shows a representative initial installation of a helical tension spring to apply a pulling force to the anterior hook 25 reacting from the posterior attachment. In the installation shown an end loop of the spring is passed through the eye 35 of the posterior attachment while the loop on the other end of the spring is secured to the anterior hook 25 by a ligature wire L. As the pulling force exerted by the spring S moves the upper first bicuspid toward the first molar, the ligature wire L will be shortened periodically to maintain continued application to the upper first bicuspid of a pulling force produced by the spring S. When the upper bicuspid has been moved toward the first molar a distance to close the gap between these teeth adequately, the anterior hook and posterior attachment can be removed. First the connecting spring S and ligature wire L will be removed, followed by removal of the anterior hook 25 and posterior attachment. It is immaterial which of the spring anchor elements is removed first.

To remove the anterior hook shown in FIGS. 18 to 31 the sequence of steps represented generally by FIGS.

21 to 31 is reversed. First the ligature wire 32 securing the anterior hook in the final position of FIGS. 30 and 31 is cut and removed so that the hook can be slid to the right from the position shown in FIGS. 30 and 31 to the position shown in FIGS. 26, 27 and 28 in which the prongs 28a and 28b have been withdrawn from their positions straddling the base 20 of the tooth bracket B. Next the hook base or plate 24 can be swiveled from the position shown in FIGS. 26, 27 and 28 through approximately 30 degrees to the position shown in FIGS. 23 and 24 when the hook shank 25' is disposed at an angle of approximately 60 degrees to the arch wire W and the slot 30 between the rear plate sections 26a and 26b is in registration with the arch wire W. The attachment can then be translated forward relative to the arch wire to withdraw the attachment from the arch wire to a position such as shown in FIG. 21 in which it will be free of the arch wire and tooth bracket assembly. Such orthodontic hook attachment can then be reused if desired.

The posterior attachment can be removed from the lower arch wire and tooth bracket assembly by following the steps generally illustrated in FIGS. 36 to 43 in reverse sequence. First the securing ligature 32 shown in FIGS. 42 and 43 will be cut and removed. Next the attachment can be shifted relative to the arch wire W from the position shown in FIGS. 40 and 41 to the position shown in FIGS. 38 and 39 which will withdraw the prongs 36a and 36b from the position straddling the body 20 of the tooth bracket. The attachment body 33 can then be swung from its position generally perpendicular to the arch wire as shown in FIGS. 38 and 39 into the canted position shown in FIGS. 36 and 37 in which the prongs 36a and 36b have cleared the arch wire. Next the attachment can be moved inward and upward relative to the arch wire to free the saddle 38, 39, 40 from the arch wire so that the attachment is completely free from the arch wire and ready to be reused as desired.

We claim:

1. A mounting for an orthodontic hook or the like capable of being installed on an arch wire and tooth bracket assembly comprising a front member for positioning in front of an arch wire and tooth bracket, a pair of generally parallel rear prongs disposed generally parallel to said front member for straddling the body of a tooth bracket behind the arch wire of the assembly when said prongs are disposed substantially parallel to the arch wire, crosstie means supporting and spacing said rear prongs from said front member in a position projecting from said crosstie means, and rearwardly-opening slot means alongside said crosstie means for receiving the arch wire only when said prongs are not substantially parallel to the arch wire to enable movement of said rear prongs from a position in front of the arch wire to a position behind the arch wire.

2. The mounting defined in claim 1, in which the front member is a plate having a tongue projecting from one edge thereof in the direction opposite the direction in which the prongs of the fork project.

3. The mounting defined in claim 2, and a projection projecting rearwardly from the tongue for overlying the arch wire.

4. The mounting defined in claim 3, in which the rearward projection includes a portion extending generally parallel to the tongue for forming with the tongue a saddle for engaging the arch wire.

5. The mounting defined in claim 3, in which the rearward projection is spaced from the fork and crosstie and a rearwardly opening slot for receiving the arch wire is formed between the rearward projection on one side and the fork and crosstie on the other side.

6. The mounting defined in claim 3, in which the fork prong nearer the rearward projection is shorter than the fork prong farther from the rearward projection.

7. The mounting defined in claim 1, in which one of the fork prongs is shorter than the other fork prong for enabling the shorter prong to pass the tooth bracket when the front member is swiveled relative to the arch wire from a position in which the prongs are at a substantial angle to the arch wire into a position where the prongs are generally parallel to the arch wire.

8. The mounting defined in claim 1, including a saddle for the arch wire supported by the front member and projecting therefrom in the direction opposite the direction in which the prongs project from the crosstie means.

9. A mounting for an orthodontic hook or the like capable of being installed on an arch wire and tooth bracket assembly comprising a front member for positioning in front of an arch wire and tooth bracket, a rear fork having prongs for straddling the body of a tooth bracket behind the arch wire of the assembly, a crosstie connecting said front member and said rear member in the direction opposite the direction in which said prongs of said fork project and engageable with the arc wire.

10. The mounting defined in claim 9, in which the bearing means includes a tongue and a projection projecting rearwardly from the tongue for overlying the arch wire.

11. The mounting defined in claim 10, in which the rearward projection includes a portion extending generally parallel to the tongue for forming with the tongue a saddle for engaging the arch wire.

12. The mounting defined in claim 10, in which the fork prong nearer the rearward projection is shorter than the fork prong farther from the rearward projection.

13. The mounting defined in claim 10, in which the rearward projection is spaced from the fork and crosstie and a rearwardly opening slot for receiving the arch wire is formed between the rearward projection on one side and the hook and crosstie on the other side.

14. A mounting for an orthodontic hook or the like comprising a front member, and means projecting rearwardly from said front member defining a rearwardly-opening wire-receiving slot for receiving an orthodontic arch wire by translation of said front member toward the arch wire only when the arch wire is in a predetermined angular position relative to said slot, said slot being unable to receive the arch wire when the arch wire is in any other angular position relative to said slot, and said means projecting rearwardly from said front member and forming two combined abutment means and sockets at opposite sides of said wire-receiving slot, respectively, said sockets opening into said rearwardly-opening wire-receiving slot and engageable by the arch wire by swiveling of said front member from the position in which said rearwardly-opening wire-receiving slot is engageable with the arch wire into a latched position in which the arch wire cannot be removed from said sockets by movement of said front member transversely of the arch wire without swiveling of said front member, said means for forming one of the combined abutment means and sockets including a fork for straddling the body of a tooth bracket associated with the arch wire.

15. The process of installing on an orthodontic arch wire and tooth bracket assembly a mounting for an orthodontic hook or the like having a front member connected to a rear prong which comprises first translating the mounting relative to the arch wire with the rear prong disposed alongside but offset from the tooth bracket and arranged at an angle to the arch wire to move the rear prong behind the arch wire, then swiveling the mounting to move the rear prong into a position substantially parallel to and behind the arch wire while still being offset from the tooth bracket, and thereafter sliding the mounting lengthwise of the arch wire with the prong disposed generally parallel to the arch wire toward the tooth bracket and thereby moving the prong into position engaging the tooth bracket behind the arch wire for preventing appreciable swiveling of the mounting relative to the arch wire.

16. The process of attaching a mounting for an orthodontic hook or the like to an arch wire and tooth bracket assembly which comprises translating the mounting toward the arch wire to position a rearwardly-opening slot in the mounting over the arch wire, thereafter swiveling the entire mounting in one direction to lodge the arch wire in an arch wire-receiving socket of the mounting fixed adjacent to and opening into the slot, and finally moving the mounting lengthwise of the arch wire to engage retaining means with a tooth bracket to prevent reverse swiveling of the mounting.

17. A mounting for an orthodontic hook or the like capable of being installed on an arch wire and tooth bracket assembly comprising a front member, two spaced means projecting rearwardly from said front member and forming therebetween a rearwardly-opening slot for receiving an orthodontic arch wire by translation of said front member toward the arch wire when said slot is in registration with the arch wire, one of said spaced means forming force-reaction abutment means engageably with the arch wire by swiveling of the mounting about an axis extending transversely of the arch wire out of the position in which said rearwardly-opening slot is in registration with the arch wire, and means including a fork for straddling the body of a tooth bracket for preventing reverse swiveling of the mounting to move said slot into registration with the arch wire.

18. The mounting defined in claim 17, in which the force-reaction abutment means includes a saddle forming a socket separate from the rearwardly-opening slot for receiving the arch wire.

19. A mounting for an orthodontic hook or the like capable of being installed on an arch wire and tooth bracket assembly comprising a front member, means fixed relative to and projecting rearwardly from said front member forming a rearwardly opening slot for receiving an orthodontic arch wire by translation of said front member toward the arch wire when said slot is in registration with the arch wire and a socket opening into said slot for receiving the arch wire from said slot by swiveling of the mounting in one direction to move said slot into a position at a substantial angle to the arch wire, and means including a prong engageable with a tooth bracket for preventing reverse swiveling of the mounting to move said slot into registration with the arch wire when said prong is engaged with such tooth bracket.

20. The process of installing on an orthodontic arch wire and tooth bracket assembly a mounting for an orthodontic hook or the like having slot-forming means and a bracket-engaging prong which comprises first translating the mounting relative to the arch wire with the slot formed by the slot-forming means in generally parallel registration with the arch wire to move the arch wire through the slot until the prong is located rearwardly of the arch wire, then swiveling the mounting relative to the arch wire to move the slot out of a position substantially parallel to the arch wire and with the prong projecting toward a tooth bracket generally parallel to the arch wire, and sliding the mounting lengthwise of the arch wire to engage the prong with the tooth bracket behind the arch wire for preventing swiveling of the mounting relative to the arch wire sufficient to place the slot formed by the slot-forming means in registration with the arch wire.

* * * * *

UNITED STATES PATENT AND TRADEMARK OFFICE
CERTIFICATE OF CORRECTION

PATENT NO. : 4,797,095

DATED : January 10, 1989

INVENTOR(S) : Armstrong et al.

It is certified that error appears in the above-identified patent and that said Letters Patent is hereby corrected as shown below:

Column 12, line 26,
  After "rear" insert -- fork, and bearing means projecting from said front --.

Column 12, line 28,
  "arc" should read -- arch --.

Column 13, line 41,
  "engageably" should read -- engageable --.

Signed and Sealed this

Twenty-fourth Day of October, 1989

Attest:

DONALD J. QUIGG

*Attesting Officer*  *Commissioner of Patents and Trademarks*